United States Patent
Scherer et al.

(10) Patent No.: US 6,319,006 B1
(45) Date of Patent: Nov. 20, 2001

(54) METHOD FOR PRODUCING A DRILL ASSISTANCE DEVICE FOR A TOOTH IMPLANT

(75) Inventors: Franz Scherer, Cologne; Joachim Pfeiffer, Bensheim, both of (DE)

(73) Assignee: Sirona Dental Systems GmbH, Bensheim (DE)

( * ) Notice: Subject to any disclaimer, the term of this patent is extended or adjusted under 35 U.S.C. 154(b) by 0 days.

(21) Appl. No.: 09/699,363

(22) Filed: Oct. 31, 2000

(30) Foreign Application Priority Data

Nov. 3, 1999 (DE) .............................. 199 52 962

(51) Int. Cl.[7] .................................................. A61C 5/00
(52) U.S. Cl. .................................... 433/215; 433/75
(58) Field of Search .............................. 433/75, 76, 173, 433/214, 215

(56) References Cited

U.S. PATENT DOCUMENTS

| 5,888,065 | 3/1999 | Sussman | 433/76 |
| 5,927,982 | * 7/1999 | Kruger | 433/213 |
| 5,967,777 | * 10/1999 | Klein et al. | 433/75 |
| 6,224,373 | * 5/2001 | Lee et al. | 433/68 |

FOREIGN PATENT DOCUMENTS

| 197 25 197 A1 | 7/1998 | (DE) . |
| WO 99/32045 | 7/1999 | (WO) . |

* cited by examiner

Primary Examiner—Cary E. O'Connor
(74) Attorney, Agent, or Firm—Dykema Gossett PLLC

(57) ABSTRACT

A method for producing a drill assistance device for a tooth implant includes the process steps of, initially the taking of an x-ray picture of the jaw and the compilation of a corresponding measured data record; then a three-dimensional, optical measurement of the visible surfaces of the jaw and of the teeth and the compilation of a corresponding measured data record. The measured data records from the x-ray picture and the measured data records from the three-dimensional, optical image are correlated with each other. Based on the information that is now available the type and position of the implant relative to the adjacent teeth is planned and a drill template is produced which is attached to the neighboring teeth, thus making the exact drilling of the implant pilot hole possible.

10 Claims, 2 Drawing Sheets

METHOD FOR PRODUCING A DRILL ASSISTANCE DEVICE FOR A TOOTH IMPLANT

BACKGROUND OF THE INVENTION

The invention relates to a method for producing a drill assistance device in order to precisely place a pilot hole for a tooth implant, wherein the pilot hole for the tooth implant is aligned relative to the teeth that still remain in the jaw.

WO 99/32045 discloses a method for producing a dental drill assistance device for tooth implants. In accordance with such method, a three-dimensional computer image is modeled using an image of the jaw relative to an imprint surface. With the computer graphics generated in this manner at least one bore hole position is determined, with the bore hole position being specified in three dimensions, including the bore hole end point and the bore hole length in relation to the jaw imprint. Subsequently, at least one set of implant bore hole coordinates is fed into a computer-controlled precision machine tool. Envisioned on a drill body is a first surface which corresponds with the imprint surface of the jaw. Using the precision machine tool, a drill guide base is prepared inside the drill body for each of the previously entered sets of bore hole coordinates with the corresponding bore hole position and bore hole orientation previously determined using the section of the jaw.

According to this known method the position and the orientation of the bore hole are determined by way of an imprint that is taken from the jaw bone. When placing tooth implants the shape and the size of the implant is exactly planned using x-ray pictures. The implant position in the jaw is predetermined with as much precision as possible. In use are drill templates which are intended to allow the placement of an exactly positioned bore hole. Ordinarily it is difficult, however, to determine the position of a pilot hole exactly during the drilling process because the information that is contained in the x-ray cannot be exactly transferred to the optical images which the physician sees while drilling. The physician relies on experience, in particular with respect to the position and the path of the nerve tracts that run along the jaw bone. Thus, we have the unsatisfactory result that, on the one hand, the implants are planned and manufactured very exactly and precise to the last detail but, on the other hand, their positioning in the jaw area has been effected to date on the basis of individual experience, which can vary considerably among different dentists.

A method and an apparatus for the localization of tooth implants and a device for the allocation of coordinates became known in the art from German published patent application 197 25 197. This method and apparatus for the localization of tooth implants process metrologically collected anatomical data reflecting the nature of the jaw bone of the respective patient. Based on the stored data sectional drawing information is generated which is used to define the implant location. Using an allocated reference system of coordinates, the actual bone geometry, the metrological information, the design of a plaster model of the jaw and the geometry of an operational assistant template can be placed in relation to one another with such a level of precision that a highly accurate placement of a bore hole in the jaw bone, which will receive the tooth implant, is supported. The transfer of the respective coordinate information to the assistance devices and processing installations that are in use is supported by a mechanical transfer element, which can, for instance, have an arc-shaped design containing an adapter that can be introduced into the mouth of the patient.

Other processes for implant bore holes in the jaw are known from U.S. Pat. No. 5,888,065 which forego a precise determination of the pilot hole position altogether.

SUMMARY OF THE INVENTION

Based on the problem outlined above and the solutions known from the state of the art, it is the object of the present invention to provide a drill assistance device that will allow the exact drilling of a pilot hole for a tooth implant in relation to the teeth that still remain in the jaw.

In accordance with the invention this objective is achieved by carrying out the following process steps during the production process for a drill assistance device for a tooth implant:

The taking of x-ray pictures of the jaw and the compilation of corresponding measured data records;

The generation of three-dimensional optical measuring data of the visible surfaces of the jaw and teeth and the compilation of a corresponding data record;

The correlation of the measured data records from the x-ray picture and of the measured data records from the three-dimensional optical measuring;

The planning of the implant type and of the implant position (location, angle), preferably using the x-ray data;

The calculation of the position (location, angle, depth) of the implant pilot hole relative to the recorded surfaces of the neighboring teeth;

The production of a drill template containing the negatives of the surfaces of the adjacent teeth and featuring an opening located at a predetermined location.

Using the method according to the invention, the x-ray and the actual optical proportions inside the patient's mouth are interconnected by linking the two images in such a way that a drill assistance device in form of a drill template can be made available which contains the pilot hole that is necessary for fastening the implant in its optimal position, based on the location of the neighboring teeth. The dentist heeds the support that is provided by the drill assistance device for the pilot hole and thus ensures that the nerve strands running inside the jaw, whose position cannot be derived from the three-dimensional surface measurement but is known nevertheless from the x-ray, will not be disturbed.

Further in accordance with the invention the x-ray can be a panoramic tomography picture, a tomosynthetic image or an image produced by means of computer tomography. Preferably the occlusal surfaces of the remaining teeth that are adjacent the implant are measured by the three-dimensional optical measuring of visible surfaces. Based on the correlation of the measured data records of the x-ray and of the measured data records of the three-dimensional optical image the visible proportions as well as the proportions that are not visible to the human eye, i.e., for example, the nerve paths, in the implant area become known and consequently allow the safe placement of a pilot hole into the jaw.

To correlate the x-ray picture with the three-dimensional optical image of the visible structures it is possible to use markers. These markers, for instance, they can be ball-shaped bodies, are visible on the x-ray as well as on the three-dimensional optical image of the jaw. By superimposing the markers the user can easily generate an interactive correlation of the x-ray picture and of the three-dimensional optical image of the visible structures.

Correlating the measured data records of the x-ray picture and of the three-dimensional optical image can also be accomplished if measured data records of the three-dimensional optical image are converted to pseudo-x-ray pictures, assuming standard x-ray absorption values. Looked at from several directions it is possible to bring the actual x-ray and the pseudo-x-ray to overlap, for example by way of longitudinal and transverse sections of the panoramic x-ray picture. A correlation can also be achieved if, at least in part, the surface shapes are extracted from the x-ray pictures as they are recorded in the optical image, and then they are superimposed with the data of the optical image. This can be accomplished automatically or interactively.

Based on the x-ray data the implant can be determined and positioned in ways that are known in the art. Using the information that was obtained with respect to the surface structure, i.e., the occlusal surfaces of neighboring teeth, it is possible to grind out on a CAD/CAM unit an implant assistance device in the form of a drill template. The shape of the still remaining adjacent teeth is represented as a negative on the drill assistance device. The drill assistance device contains a bore hole which serves as a drill guide for the dentist's drill in order to create the bore hole that is used to fasten the implant. The negative forms of the occlusal surfaces allow the unmistakable positioning of the drill template inside the mouth of the patient.

DETAILED DESCRIPTION OF THE INVENTION

Figure 1:
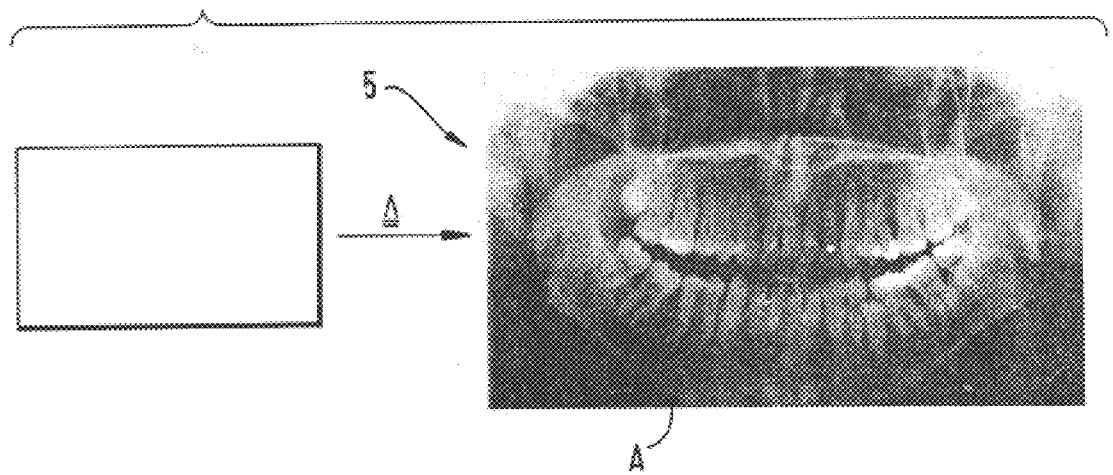
FIG. 1 is a panoramic tomography picture in schematic form.

FIG. 1 shows a thoroughly schematized x-ray as well as an x-ray picture in the form of a panoramic tomography image depicting the upper and lower jaw areas in a plane representation. Instead of a panoramic tomography image a tomosynthetic x-ray or a computer tomography x-ray can be generated and made available.

Figure 2:
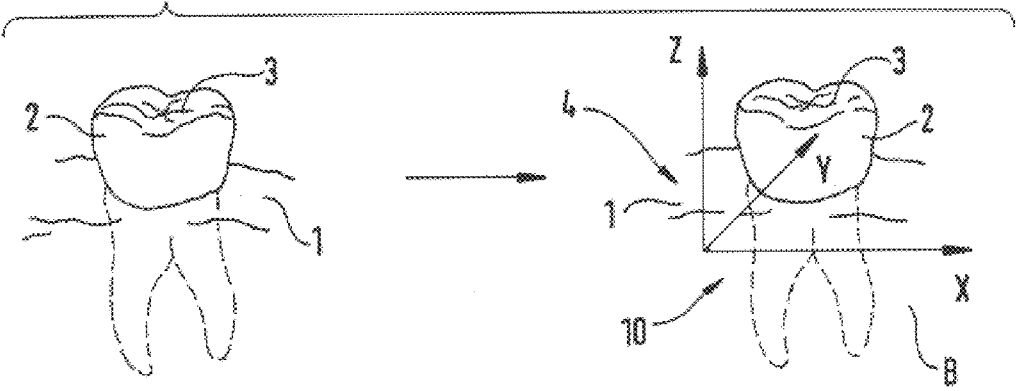
FIG. 2 shows the generation of a three-dimensional optical image of visible structures in the jaw.

FIG. 2 is a schematized depiction of a three-dimensional image of a molar 2 on which the surface structure, the occlusal surface 3, is measured using a three-dimensional system of coordinates 4. In addition to measuring molar 2, as shown, it is also possible to measure an entire jaw branch, either in the upper jaw or in the lower jaw. The x-ray picture 5 and/or the three-dimensional optical image 10 can be stored and filed as measured data records; and the respective measured data records for the image 5, 10 can be correlated using certain predetermined criteria.

Figure 3:
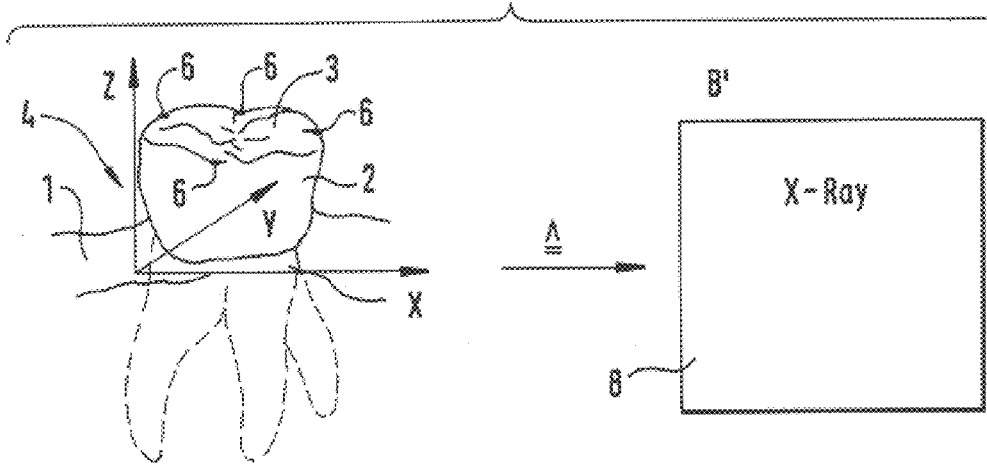
FIG. 3 shows the generation of a pseudo-x-ray based on a three-dimensional image of visible structures.
Figure 4:
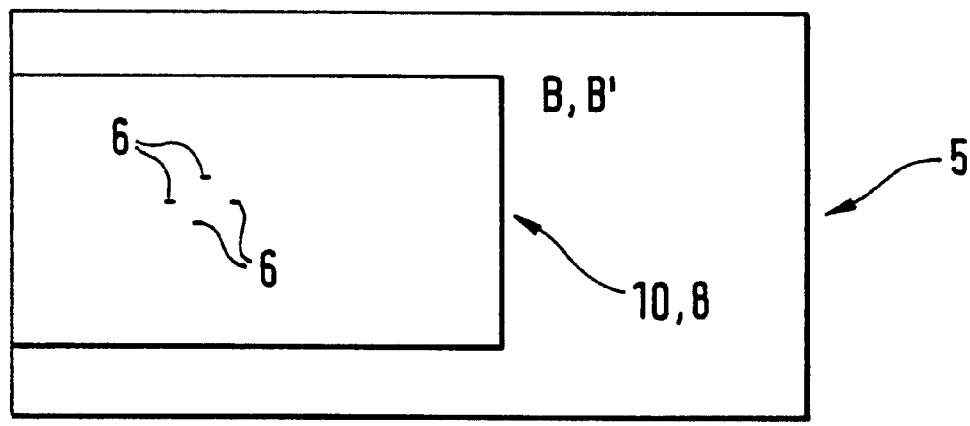
FIG. 4 shows the superposition of the x-ray picture and the three-dimensional optical image or the pseudo-x-ray image B'.

By way of correlation, which can be achieved in different ways, the invisible realities of the implant location, i.e., those proportions that the human eye cannot perceive, are linked with realities that the dentist is able to discern. On the one hand, the correlation can be accomplished by superimposing an x-ray picture A and a three-dimensional image B (refer to FIG. 4) using markers 6, that are attached to the teeth 2 (FIG. 3), in order to create fixed points that make it possible to superimpose an x-ray picture A and a three-dimensional image B. Thus a correlation of the two measured data records can take place. Instead of the markers 6 that can be fastened to the teeth 2 it is possible to generate a pseudo-x-ray B', 8, based on the surface data of the three-dimensional image 10, while assuming standard x-ray absorption values and generation theory for the respective x-ray. In an interactive step the user can bring the available x-ray 5 and pseudo-x-ray 8 to overlap. If the user undertakes the correlation from several directions, the correlation of the x-ray picture 5 with the three-dimensional image 10 is complete. If a panoramic tomography image is used as the x-ray picture, the user can correlate the two by way of sections running in longitudinal and transverse directions through the panoramic tomography image. Thus, the X- and Y-directions of the system of coordinates 4 are covered.

Figure 5:
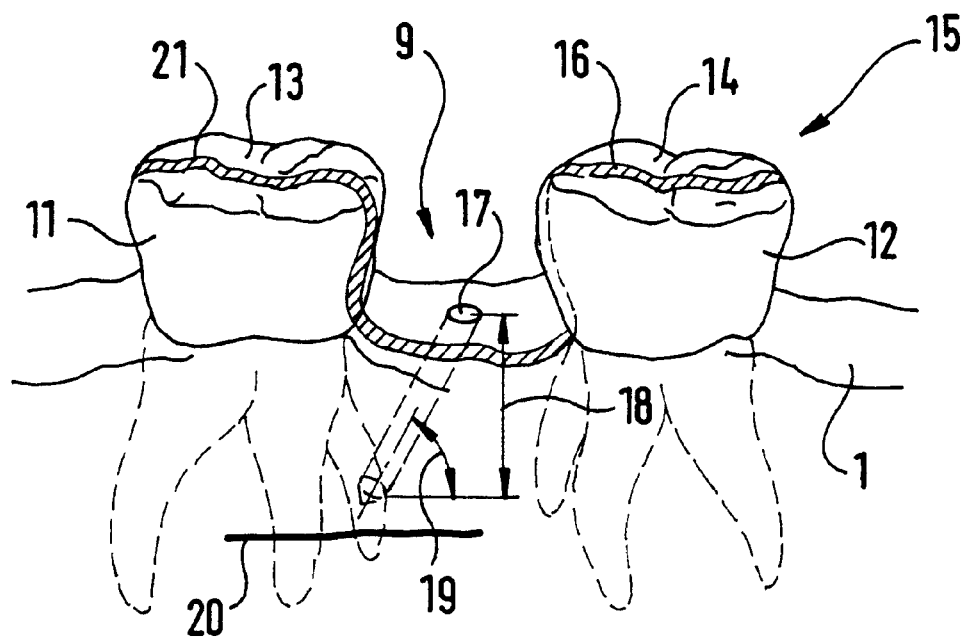
FIG. 5 shows the space between two neighboring teeth that is envisioned for the implant and a drill assistance device located in that space.

The position of the implant is planned in the x-ray picture according to FIG. 1, and the position in the jaw 1 is determined from one, ordinarily, however, from two directions. From the x-ray A, reference designation 5, the path of the nerve 20 in the lower area of the jaw 1 is known, and based on the position of the nerve the depth of the bore hole 18 can be planned (refer to FIG. 5). The correlation of the x-ray picture 5 with the three-dimensional optical image 10 permits taking into consideration the teeth 11 and 12 which are arranged adjacent to the implant position 9. The position of these teeth is known based on the x-ray picture 5 as well as based on the three-dimensional optical image 10. Moreover, from the three-dimensional optical image 10 there also result the occlusal surface structures 13 and 14 of the neighboring teeth 11 and 12. Since the x-ray and the 3-D image are correlated relative to each other, the position of the planned implant relative to the occlusal surfaces of the neighboring teeth is known. Therefore, it is possible to establish the location of the bore hole and the depth of the bore hole.

By entering continuous lines the user can now determine the size of the bore hole template. Using the measured data, a CAD/CAM machine is able to produce the bore hole template including the negatives for the occlusal surfaces and a guide path for the drill.

The drill assistance device 16 that was obtained in such a manner is secured onto the occlusal surfaces 13 and 14 of the adjacent teeth 11 and 12, which form the limits to the implant position 9, by means of a dissolvable adhesion layer 21. The drill assistance device 16 or the drill template can be produced advantageously by means of a precision machine tool that can be operated three-dimensionally, and which is also suitable for producing dental prostheses.

The exact positioning of the drill assistance device 16 relative to the jaw section 15 of the implant position 9 is accomplished in that the negative form of the drill assistance device 16 attaches on the occlusal surfaces 13, 14 of the neighboring teeth 11 and 12. The position of the pilot hole 17 is predetermined on the surface of the drill assistance device as is the angle 19 in which the dentist has to apply the drill. The dentist determines the depth of the bore hole 18 based on the correlation of the measured data records from x-ray picture 5, either available as panoramic tomography image or as a tomosynthetic image, and transfers the depth to the drill template as a stop.

Since the pilot hole 17 is positioned on the top side of the drill assistance device 16 the dentist can carry out the drilling operation in the jaw 1 secure in the knowledge of having chosen the optimal pilot hole position for fastening the implant between the adjacent teeth 11 and 12.

What is claimed is:

1. Method for producing a drill assistance device for a tooth implant in a person's jaw, comprising the following process steps:

taking an x-ray picture of the jaw and compiling a corresponding measured data record, carrying out a three-dimensional optical measuring of the visible surfaces of the jaw and of the teeth and compiling a corresponding measured data record, correlating the measured data records from the x-ray picture and from the measured data records of the three-dimensional optical measuring, determinating the optimal bore hole for the implant, based on the x-ray picture, and determinating a pilot hole in a drill template relative to surfaces of the neighboring teeth based on the x-ray picture and optical measurement.

2. The method according to claim 1, wherein the x-ray picture is one of a panoramic tomography image, a tomosynthetic image or a computer tomography image.

3. The method according to claim 1, wherein the three-dimensional, measured, visible surfaces are the occlusal surfaces of neighboring teeth located on the jaw.

4. The method according to claim 1, wherein the correlation of the measured data records from the x-ray picture and from the three-dimensional optical image is carried out by the provision of markers attached to the teeth.

5. The method according to claim 4, wherein the marker comprises a ball shaped body.

6. The method according to claim 1, wherein the measured data records of the three-dimensional measurement are converted to a pseudo-x-ray picture, assuming standard x-ray absorption values and the generation theory of the respective x-ray image.

7. The method according to claim 6, wherein the x-ray picture and the pseudo-x-ray picture are superimposed from several directions.

8. The method according to claim 7, wherein the x-ray picture comprises at least two individual panoramic images showing longitudinal and transverse sections of the jaw.

9. The method according to claim 1, wherein the drill assistance device is ground out from a dimension-stable material, and said material represents the form of occlusal surfaces of neighboring teeth as a negative with respect to an implant position.

10. The method according to claim 9, wherein the drill assistance device contains a bore hole position that serves as a guide for the drill.

* * * * *